US010555977B2

(12) United States Patent
Anglenius et al.

(10) Patent No.: US 10,555,977 B2
(45) Date of Patent: Feb. 11, 2020

(54) PROBIOTIC BACTERIA FOR THE TOPICAL TREATMENT OF SKIN DISORDERS

(71) Applicant: DUPONT NUTRITION BIOSCIENCES APS, Copenhagen (DK)

(72) Inventors: Heli Anglenius, Kirkkonummi (FI); Kirsti Tiihonen, Helsinki (FI); Nina Rautonen, Espoo (FI); Arthur Ouwehand, Ingå (FI)

(73) Assignee: DuPont Nutrition Biosciences ApS (DK)

( * ) Notice: Subject to any disclaimer, the term of this patent is extended or adjusted under 35 U.S.C. 154(b) by 0 days.

(21) Appl. No.: 15/963,493

(22) Filed: Apr. 26, 2018

(65) Prior Publication Data

US 2019/0099454 A1    Apr. 4, 2019

Related U.S. Application Data

(63) Continuation of application No. 14/860,836, filed on Sep. 22, 2015, now abandoned, which is a continuation of application No. 14/114,591, filed as application No. PCT/EP2012/058047 on May 2, 2012, now abandoned.

(30) Foreign Application Priority Data

May 3, 2011 (EP) .................... 11164534

(51) Int. Cl.
*A61K 35/741* (2015.01)
*A61K 31/205* (2006.01)
*A61K 35/745* (2015.01)
*A61K 35/747* (2015.01)
*A61K 35/744* (2015.01)

(52) U.S. Cl.
CPC .......... *A61K 35/741* (2013.01); *A61K 31/205* (2013.01); *A61K 35/744* (2013.01); *A61K 35/745* (2013.01); *A61K 35/747* (2013.01)

(58) Field of Classification Search
None
See application file for complete search history.

(56) References Cited

U.S. PATENT DOCUMENTS 6,455,063 B1 *  9/2002  Rehberger ............ A61K 35/74
                                                          424/438
2003/0049231 A1    3/2003  Baur 2005/0196480 A1    9/2005  Sullivan
2008/0107699 A1 *  5/2008  Spigelman ............ A01N 63/00
                                                          424/404
2009/0068160 A1 *  3/2009  Castiel ................. A61Q 19/005
                                                          424/93.42
2009/0311227 A1 * 12/2009  Ouwehand ........... A61K 31/352
                                                          424/93.45

FOREIGN PATENT DOCUMENTS

| EP | 1 787 651 A1 | 5/2007 |
| EP | 2 226 068 A1 | 9/2010 |
| GB | 2466195 A | 6/2010 |
| WO | WO 2005/030230 A1 | 4/2005 |
| WO | WO 2006/013441 A2 | 2/2006 |
| WO | WO 201 0/01 31 7 | 2/2010 |

OTHER PUBLICATIONS

Cork et al. 2005 (Predisposition to sensitive skin and atopic eczema; Community practitioner 2005; 78, 12: 440-442). (Year: 2005).*
Putaala et al. 2008 (Effect of four probiotic strains and Escherichia coli O157:H7 on tight junction integrity and cyclo-oxygenase expression; Research in Microbiology 159: 692-698) (Year: 2008).*
International Preliminary Report on Patentability, International Application No. PCT/EP2012/058047, International Filing Date May 2, 2012.
Written Opinion of the International Searching Authority, International Application No. PCT/EP2012/058047, International Filing Date May 2, 2012.
International Search Report, International Application No. PCT/EP2012/058047, International Filing Date May 2, 2012.
Cereijido et al., "New Diseases Derived or Associated with the Tight Junction", Archives of Medical Research 38 (2007) 465-478.
Albertini, B., et al., "Development of microparticulate systems for intestinal delivery of *Lactobacillus acidophilus* and *Bifidobacterium lactis*," *Eur J of Pharm Sciences*, 2010, vol. 40, pp. 359-366.
Bär, M., et al., "Selection and Validation of Candidate Housekeeping Genes for Studies of Human Keratinocytes-Review and Recommendations," *Journal of Investigative Dermatology*, 2009, vol. 129, pp. 535-537.
Brandner, J. M., "Tight junctions and tight junction proteins in mammalian epidermis," *Eur J of Pharm and Biopharm*, 2009, vol. 72, pp. 289-294.

(Continued)

*Primary Examiner* — Mary Maille Lyons (57) ABSTRACT

The present invention relates to a probiotic bacteria, and/or soluble metabolite of a probiotic bacteria and/or a cell lysate of a probiotic bacteria for use in the treatment of a disorder associated with Tight Junction function, characterised in that the probiotic bacteria, soluble metabolite of a probiotic bacteria and/or a cell lysate of a probiotic bacteria is formulated for topical administration.

23 Claims, 6 Drawing Sheets

(56) References Cited

OTHER PUBLICATIONS

Chen, Y.-H., et al., "Nonreceptor Tyrosine Kinase c-Yes Interacts with Occludin during Tight Junction Formation in Canine Kidney Epithelial Cells," *Mol Biol Cell*, 2002, vol. 13, pp. 1227-1237.
Danisco Technical Memorandum, 2012.
Davis, C., and J.A. Milner, "Gastrointestinal microflora, food components and colon cancer prevention," *Journal of Nutritional Biochemistry*, 2009, vol. 20, pp. 743-752.
FloraFit® Custom Probiotics Strain Information Sheet, 2012.
Furuse, M., et al., "Claudin-based tight junctions are crucial for the mammalian epidermal barrier: a lesson from claudin-l-deficient mice," *J Cell Biol*, 2002, vol. 156, pp. 1099-1111.
Honari, S., et al., "Topical therapies and antimicrobials in the management of burn wounds," *Crit Care Nurs Clin N Am*, 2004, vol. 16, pp. 1-11.
Livak, K. J. and Schmittgen, T. D., "Analysis of Relative Gene Expression Data Using Real-Time Quantitative PCR and the 2-cT Method," *Methods*, 2001, vol. 25, pp. 402-408.
Minner, F., et al., "Candidate Housekeeping Genes Require Evaluation before their Selection for Studies of Human Epidermal Keratinocytes," Journal of Investigative Dermatology, 2009, vol. 129, pp. 770-773.
Neville, B. A. and O'Toole, P. W., "Probiotic properties of *Lactobacillus salivarius* and closely related *Lactobacillus* species," *Future Microbiol*, 2010, vol. 5, No. 5, pp. 759-774.
Nicander, I., et al., "The ability of betaine to reduce the irritating effects of detergents assessed visually, histologically and by bioengineering methods," *Skin Res and Technology*, 2003, vol. 9, pp. 50-58.
Ouwehand, A. C., et al., "Influence of a combination of *Lactobacillus acidophilus* NCFM and lactitol on healthy elderly: intestinal and immune parameters," *British Journal of Nutrition*, 2009, vol. 101, pp. 367-375.
Ouwehand, A. C., et al., "Specific probiotics alleviate allergic rhinitis during the birch pollen season," *World J Gastroenterol*, 2009, vol. 15, No. 26, pp. 3261-3268.
Pummi, K., et al., "Epidermal Tight Junctions: ZO-1 and Occludin are Expressed in Mature, Developing, and Affected Skin and In Vitro Differentiating Keratinocytes," *Invest Dermatol*, 2001, vol. 117, pp. 1050-1058.
Putaala, H., et al., "Effect of four probiotic strains and *Escherichia coli* O157:H7 on tight junction integrity and cyclo-oxygenase expression," *Res in Microbiol*, 2008, vol. 159, pp. 692-698.
Saitou, M., et al., "Complex Phenotype of Mice Lacking Occludin, a Component of Tight Junction Strands," *Mol Biol Cell*, 2000, vol. 11, pp. 4131-4142.
Sanders, M. E., et al., "*Invited Review*: The Scientific Basis of *Lactobacillus acidophilus* NCFM Functionality as a Probiotic," *J Dairy Sci*, 2001, vol. 84, pp. 319-111.
Sousa, S., et al., "Microbial strategies to target, cross or disrupt epithelia," *Curr Opinion in Cell Biol*, 2005, vol. 17, pp. 489-498.
Ukena, S. N., et al., "Probiotic *Escherichia coli* Nissle 1917 Inhibits Leaky Gut by Enhancing Mucosal Integrity," *PLoS One*, 2007, Issue 12, e1308.
Van Itallie, C. M., et al., "ZO-1 Stabilizes the Tight Junction Solute Barrier through Coupling to the Perijunctional Cytoskeleton," *Mol Biol Cell*, 2009, vol. 20, pp. 3930-3940.
Yamamoto, T., et al., "Relationship between expression of tight junction-related molecules and perturbed epidermal barrier function in UVB-irradiated hairless mice," *Arch Dermatol Res*, 2008, vol. 300, pp. 61-68.
Yamamoto, T., et al., "Effect of RNA interference of tight junction-related molecules on intercellular barrier function in cultured human keratinocytes," *Arch Dermatol Res*, 2008, vol. 300, pp. 517-524.
Anderson et al. 2010 (Lactobacillus plantarum MB452 enhances the function of the intestinal barrier by increasing the expression levels of genes involved in tight junction formation; BMC Microbiology 10:316).
Putaala et al. 2012 (Probiotics modulate tight junction integrity and expression of junctional proteins in cultured normal human epidermal keratinocytes; International Journal of Probiotics and Prebiotics 7(2): 81-90; see abstract and Figure 1).
Cork, et al., "Predisposition to sensitive skin and atopic eczema" Community practitioner, 2005, vol. 78, No. 12, pp. 440-442.

\* cited by examiner

PROBIOTIC BACTERIA FOR THE TOPICAL TREATMENT OF SKIN DISORDERS

CROSS-REFERENCE TO RELATED APPLICATIONS

This application is a continuation under 35 U.S.C. § 120 of U.S. application Ser. No. 14/860,836 (filed Sep. 22, 2015), which is a continuation under 35 U.S.C. § 120 of U.S. application Ser. No. 14/114,591 (filed Oct. 29, 2013), which is the U.S. National Stage under 35 USC § 371 of International Application PCT/EP2012/058047 (filed May 2, 2012), which designates the U.S. and was published by the International Bureau in English on Nov. 8, 2012, and which claims the benefit of European Application No. 11164534.7 (filed May 3, 2011). The entire text of each of the foregoing applications is hereby incorporated by reference into this patent.

FIELD OF INVENTION

The present invention relates to probiotic bacteria and/or soluble metabolites of a probiotic bacteria and/or a cell lysate of a probiotic bacteria for use in the topical treatment of a disorder associated with skin barrier function.

BACKGROUND OF THE INVENTION

The epidermis, the squamous stratified epithelium of the skin, consists of multiple sublayers and is one of the most important barriers of the body with the outside world. Stratum corneum is the outermost layer of the epidermis and the final anucleated step in keratinocyte differentiation from the cells in nucleated epidermal layers. Although stratum corneum is recognised as the most important physical barrier, the nucleated epidermal layers are also significant in barrier function as evidenced by studies with burn victims (1, 2). Together, the skin barrier protects against extensive water loss in one direction (inside-outside barrier) and against the invasion of harmful substances from the environment (outside-inside barrier) (2). The maintenance of the barrier is also important for balanced proliferation in the basal layer and preservation of the calcium ion gradient and thus proper epidermal differentiation (3).

In the mammalian epidermis, tight junctions (TJ) are mainly found in the stratum granulosum, or the granular layer of the epithelium, located underneath the stratum corneum (4). TJ are dynamic cell-cell junctions that connect neighbouring cells, control the paracellular pathway of molecules acting as barriers, and have a fence function by separating apical cell membranes from basolateral cell membranes (5). They are important not only in inside-outside barrier function but also in outside-inside barrier function.

Probiotics have been defined as "live microorganisms, which when administered in adequate amounts, confer health benefit on the host" (13). Research of the effects of oral administration of probiotics on the epidermis has previously been undertaken. Probiotics have been suggested to modulate the immunity systemically and have been suggested for prophylactic use to alleviate atopic eczema in children (17).

Few studies have been undertaken to study how probiotics affect keratinocytes when administered topically. However, in one study, sonicated lysates of Streptococcus thermophilus have been observed to increase the level of ceramides in stratum corneum in vitro and in vivo (22).

SUMMARY OF THE INVENTION

The present invention is based on the inventors surprising discovery that topical administration of probiotic bacteria, and/or soluble metabolites of probiotic bacteria and/or a cell lysates of probiotic bacteria can improve Tight Junction (TJ) function in the epithelium.

The importance of the role of TJ as part of the epidermal barrier function of the skin has been verified by discovering that deficiency of the TJ protein claudin 1 (cldn-1) results in fatal epidermal water-loss in neonate mice (4). In various skin diseases with perturbed barrier function, such as psoriasis, zonula occludens protein 1 (ZO-1) and occludin are relocalised to the lower epidermal layers (6). TJ proteins are also known to be targets for bacterial, and viral insults, and certain viruses and bacteria use them as receptors in pathogenesis (8). Moreover, allergens may disrupt TJ and promote asthma (9). In addition, UV-induced epidermal barrier perturbation is associated with TJ barrier impairment (10). Therefore, TJ are important not only in inside-outside barrier but also in outside-inside barrier.

Therefore, according to a first broad aspect of the present invention there is provided a probiotic bacteria, and/or soluble metabolites of a probiotic bacteria and/or a cell lysate of a probiotic bacteria for use in the treatment of a disorder associated with Tight Junction function, characterised in that the probiotic bacteria, soluble metabolite of a probiotic bacteria and/or a cell lysate of a probiotic bacteria is formulated for topical administration.

According to a second aspect of the present invention there is provided a method of treating a patient suffering from a disorder associated with Tight Junction function comprising topically administering to a patient a probiotic bacteria, and/or soluble metabolites of a probiotic bacteria and/or a cell lysate of a probiotic bacteria.

According to a third aspect of the present invention there is provided the use of a probiotic bacteria, and/or soluble metabolites of a probiotic bacteria and/or a cell lysate of a probiotic bacteria in the manufacture of a topical medicament for use in the treatment of a disorder associated with Tight Junction function.

DETAILED DESCRIPTION OF THE INVENTION

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range.

Other definitions of terms may appear throughout the specification. Before the exemplary embodiments are described in more detail, it is to understand that this disclosure is not limited to particular embodiments described. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that such publications constitute prior art to the claims appended hereto.

It will be understood that in the following, preferred embodiments referred to in relation to one broad aspect of the invention are equally applicable to each of the other broad aspects of the present invention described above. It will be further understood that, unless the context dictates otherwise, the preferred embodiments described below may be combined.

When used herein, the term topical includes references to formulations that are adapted for application to body surfaces (e.g. the skin or mucous membranes). Mucous membranes that may be mentioned in this respect include the mucosa of the vagina, the penis, the urethra, the bladder, the anus, the mouth (including the mucosa of the cheek, the soft palate, the under surface of tongue and the floor of the mouth), the nose, the throat (including the mucosa of the pharynx, the larynx, the trachea and the esophagus), the bronchi, the lungs, the eye and the ear.

In preferred embodiments of the present invention, the probiotic bacteria, soluble metabolite and/or cell lysate is formulated for administration to the skin.

It will be further understood that the formulation for use in the present invention may comprise one or more of at least one probiotic bacteria, at least one soluble metabolite of a probiotic bacteria and/or at least one cell lysate of a probiotic bacteria.

It will be further understood that the formulation may comprise more than one probiotic bacteria, soluble metabolite and/or cell lysate. For example the formulation may comprise at least 2, 3, 4, 5, 6, 7, 8, 9, 10, 12, 15 or 20 probiotic bacteria or their soluble metabolites or cell lysates.

It will be understood by the skilled person that as used herein the term probiotic refers to a live microorganism (including bacteria or yeasts for example) which, when topically applied in sufficient numbers, beneficially affects the host organism, i.e. by conferring one or more demonstrable health benefits on the host organism.

It will also be readily apparent that the formulations of the present invention may further include one or more prebiotics.

Whilst there are no lower or upper limits for probiotic use, it has been suggested that at least $10^6$-$10^{12}$, preferably at least $10^6$-$10^{10}$, preferably $10^8$-$10^9$, cfu as a daily dose will be effective to achieve the beneficial health effects in a subject.

As used herein, the term "soluble metabolite" refers to a metabolite or metabolites present in the supernatant of a cell culture from which the cells have been removed. In preferred embodiments the culture is grown to a cell density of at least about $OD_{600}$ 0.5. In a further preferred embodiment the cells are removed by centrifugation. In a more preferred embodiment the supernatant is filtered. It will be apparent that the supernatant may be used directly in the formulations of the present invention, or that one or more of the metabolites may be isolated form the supernatant by any suitable means prior to use.

As used herein, the term "cell lysate" or "lysate" refers to probiotic cells which have been lysed by any suitable means. In preferred embodiments, the cell debris is removed prior to use. In more preferred embodiments the cell lysates are filtered prior to use. In exemplary embodiments, the cells are lysed by, for example sonication, homogenisation, shearing or chemical lysis.

Probiotic bacteria suitable for use in the present invention include, but are not limited to, *Bifidobacterium, Brevibacterium, Propionibacterium, Lactococcus, Streptococcus, Lactobacillus* (e.g., *L. acidophilus*), *Enterococcus, Pediococcus, Leuconostoc,* and/or *Oenococcus.*

Soluble metabolites for use in the present invention include, but are not limited to, soluble metabolites from *Bifidobacterium, Brevibacterium, Propionibacterium, Lactococcus, Streptococcus, Lactobacillus* (e.g., *L. acidophilus*), *Enterococcus, Pediococcus, Leuconostoc,* and/or *Oenococcus.*

Cell lysates for use in the present invention include, but are not limited to, cell lysates from *Bifidobacterium, Brevibacterium, Propionibacterium, Lactococcus, Streptococcus, Lactobacillus* (e.g., *L. acidophilus*), *Enterococcus, Pediococcus, Leuconostoc,* and/or *Oenococcus.*

Preferably, the probiotic bacteria, soluble metabolite and/or cell lysate for use according to the present invention comprises at least one lactic acid bacteria.

More preferably, the probiotic bacteria, soluble metabolite and/or cell lysate is selected from the group comprising *Lactobacillus acidophilus, Lactobacillus salivarius, Bifidobacterium lactis* and *Propionibacterium jensenii.*

In an even more preferred embodiment the bacteria or cell lysate is selected from *Lactobacillus acidophilus* NCFM, *Lactobacillus salivarius* Ls-33 and *P. jensenii* P63.

In an alternative preferred embodiment the soluble metabolite of a probiotic bacteria is from *Bifidobacterium lactis* 420.

In one preferred embodiment of the present invention, the formulation further comprises at least one of betaine, a polyol (e.g. xylitol or lactitol) and/or a polyphenol (e.g. epicatechin or gallocatechin).

It will be understood that the disorder may be any disorder associated with Tight Junction function. In preferred embodiments the disorder is selected from the group comprising psoriasis, acne, atopic dermatitis, dry skin, allergy, rashes, UV-irritated skin, detergent irritated skin (including irritation caused by enzymes used in washing detergents and sodium lauryl sulphate), thinning skin (e.g. skin from the elderly and children).

It will be further apparent that the formulation for use according to the present invention may comprise any pharmaceutically effective amount of the probiotic bacteria, soluble metabolite and/or cell lysate, for example, at least about 0.01%, about 0.05%, about 0.1%, about 0.2%, about 0.3%, about 0.4%, about 0.5%, about 0.6%, about 0.7%, about 0.8%, about 0.9%, about 1.0%, about 1.5%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 20.0%, about 25.0%, about 30.0%, about 35.0%, about 40.0%, about 45.0%, about 50.0% by weight of probiotic bacteria, soluble metabolite and/or cell lysate.

In an alternative embodiment the formulation for use according to the present invention may comprise, for example, at least about 0.01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to about 5%, by weight of probiotic bacteria, soluble metabolite and/or cell lysate.

The topical formulation for use in the present invention may be in any form suitable for application to the body surface, such as a cream, lotion, sprays, solution, gel, ointment, paste, plaster, paint, bioadhesive, suspensions or the like, and/or may be prepared so as to contain liposomes, micelles, and/or microspheres. Such a formulation may be used in combination with an occlusive overlayer so that moisture evaporating from the body surface is maintained within the formulation upon application to the body surface and thereafter.

Topical formulations include those in which the active ingredient(s) is (are) dissolved or dispersed in a dermatological vehicle known in the art (e.g. aqueous or non-aqueous gels, ointments, water-in-oil or oil-in-water emulsions). Constituents of such vehicles may comprise water, aqueous buffer solutions, non-aqueous solvents (such as ethanol, isopropanol, benzyl alcohol, 2-(2-ethoxyethoxy) ethanol, propylene glycol, propylene glycol monolaurate, glycofurol or glycerol), oils (e.g. a mineral oil such as a liquid paraffin, natural or synthetic triglycerides such as Miglyol™, or silicone oils such as dimethicone). Depending, inter alia, upon the nature of the formulation as well as its intended use and site of application, the dermatological vehicle employed may contain one or more components (for example, when the formulation is an aqueous gel, components in addition to water) selected from the following list:

a solubilising agent or solvent (e.g. a β-cyclodextrin, such as hydroxypropyl β-cyclodextrin, or an alcohol or polyol such as ethanol, propylene glycol or glycerol);

a thickening agent (e.g. hydroxyethylcellulose, hydroxypropylcellulose, carboxymethylcellulose or carbomer);

a gelling agent (e.g. a polyoxyethylene-polyoxypropylene copolymer);

a preservative (e.g. benzyl alcohol, benzalkonium chloride, chlorhexidine, chlorbutol, a benzoate, potassium sorbate or EDTA or salt thereof); and pH buffering agent(s) (such as a mixture of dihydrogen phosphate and hydrogen phosphate salts, or a mixture of citric acid and a hydrogen phosphate salt).

In particular compositions,
(i) water may be present at from 55 to 75% (e.g. from 60 to 72.5%) by weight;
(ii) the one or more polar, non-aqueous solvents may (together) be present at from 15 to 40% (e.g. from 24 to 35%) by weight;
(iii) glycerol, if used, may be present at from 5 to 25% (e.g. from 15 to 20%) by weight;
(iv) ethanol, if used, may be present at from 3 to 10% (e.g. from 5 to 8%) by weight;
(v) propylene glycol, if used, may be present at from 2 to 15% (e.g. from 4 to 6%) by weight;
(vi) the preservative may be present at from 0.1 to 3% (e.g. about 1%) by weight;
(vii) the thickening agent may be present at from 1 to 5% (e.g. about 2% by weight).

In further particular topical compositions, the pH buffering agent(s) may, if employed and when dissolved in the water component of the composition, provide a pH in the range of 5 to 7 (e.g. about pH 5.5).

Methods of producing topical pharmaceutical compositions such as creams, ointments, lotions, sprays and sterile aqueous solutions or suspensions are well known in the art. Suitable methods of preparing topical pharmaceutical compositions are described, for example in WO 95/10999, U.S. Pat. No. 6,974,585, WO 2006/048747 (incorporated herein by reference), as well as in documents cited in any of these references.

A pharmaceutically acceptable carrier may also be incorporated in the formulation of the present invention and may be any carrier conventionally used in the art. Examples thereof include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such carriers.

The term "pharmaceutically acceptable" or "pharmaceutically acceptable carrier" is used herein to refer to a compound or composition that may be incorporated into a pharmaceutical formulation without causing undesirable biological effects or unwanted interaction with other components of the formulation.

"Carriers" or "vehicles" as used herein refer to carrier materials suitable for incorporation in a topically applied composition. Carriers and vehicles useful herein include any such materials known in the art, which are non toxic and do not interact with other components of the formulation in which it is contained in a deleterious manner.

The term "aqueous" refers to a formulation that contains water or that becomes water-containing following application to the skin or mucosal tissue.

The pharmaceutical formulation of the invention comprises a pharmaceutically acceptable topical carrier and an active agent that consists essentially of a probiotic bacteria and/or metabolites of a probiotic bacteria and or a cell lysate of a probiotic bacteria.

Formulations of the invention may optionally contain a pharmaceutically acceptable viscosity enhancer and/or film former. A viscosity enhancer increases the viscosity of the formulation so as to inhibit its spread beyond the site of application. Balsam Fir (Oregon) is an example of a pharmaceutically acceptable viscosity enhancer.

A film former, when it dries, forms a protective film over the site of application. The film inhibits removal of the active ingredient and keeps it in contact with the site being treated. An example of a film former that is suitable for use in this invention is Flexible Collodion, USP. As described in *Remington: The Science and Practice of Pharmacy,* 19th Ed. (Easton, Pa.: Mack Publishing Co., 1995), at page 1530, collodions are ethyl ether/ethanol solutions containing pyroxylin (a nitrocellulose) that evaporate to leave a film of pyroxylin. A film former may act additionally as a carrier. Solutions that dry to form a film are sometimes referred to as paints.

Creams, as is well known in the arts of pharmaceutical formulation, are viscous liquids or semisolid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Lotions, are preparations to be applied to the skin surface without friction, and are typically liquid or semiliquid preparations in which particles, including the active agent, are present in a water or alcohol base. Lotions are usually suspensions of solids, and preferably, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Solutions are homogeneous mixtures prepared by dissolving one or more chemical substances (solutes) in a liquid such that the molecules of the dissolved substance are dispersed among those of the solvent. The solution may contain other pharmaceutically or cosmetically acceptable chemicals to buffer, stabilize or preserve the solute. Common examples of solvents used in preparing solutions are ethanol, water, propylene glycol or any other acceptable vehicles.

As is of course well known, gels are semisolid, suspension-type systems. Single-phase gels contain organic macromolecules distributed substantially uniformly throughout the carrier liquid, which is typically aqueous, but also, preferably, contain an alcohol, and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Ointments, as also well known in the art, are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, nonirritating, and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, acetyl alcohol, glyceryl monostearate, lanolin, and stearic acid. Preferred water-soluble ointment bases are prepared from polyethylene glycols of varying molecular weight; again, see Remington: The Science and Practice of Pharmacy for further information.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having a lipid wall comprising a lipid bilayer, and, in the present context, encapsulate one or more components of the formulations. Liposomal preparations herein include cationic (positively charged), anionic (negatively charged), and neutral preparations. Cationic liposomes are readily available. For example, N[1-2,3-dioleyloxy)propyl]-N,N,N-triethyl-ammonium (DOTMA) liposomes are available under the tradename Lipofectin® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoyl-phosphatidyl choline (DOPC), dioleoylphosphatidyl glycerol (DOPG), and dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl-8 dodecyl ether, polyoxyl-12 dodecyl ether, nonoxynol 10, and nonoxynol 30.

Microspheres, similarly, may be incorporated into the present formulations. Like liposomes and micelles, microspheres essentially encapsulate one or more components of the present formulations. They are generally although not necessarily formed from lipids, preferably charged lipids such as phospholipids. Preparation of lipidic microspheres is well known in the art and described in the pertinent texts and literature.

Various additives, known to those skilled in the art, may be included in the topical formulations. For example, solvents, including relatively small amounts of alcohol, may be used to solubilize certain formulation components. With particularly severe skin conditions it may be desirable to include an added permeation enhancer in the formulation.

Examples of suitable enhancers include, but are not limited to, ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer® (231, 182, 184), Tween® (20, 40, 60, 80), and lecithin (U.S. Pat. No. 4,783,450); alcohols such as ethanol, propanol, octanol, benzyl alcohol, and the like; polyethylene glycol and esters thereof such as polyethylene glycol monolaurate (PEGML; see, e.g., U.S. Pat. No. 4,568,343); amides and other nitrogenous compounds such as urea, dimethylacetamide (DMA), is dimethylformamide (DMF), 2-pyrrolidone, 1-methyl-2-pyrrolidone, ethanolamine, diethanolamine, and triethanolamine; terpenes; alkanones; and organic acids, particularly citric acid and succinic acid. Azone® and sulfoxides such as DMSO and $C_{10}MSO$ may also be used, but are less preferred.

Most preferred enhancers are those lipophilic co-enhancers typically referred to as "plasticizing" enhancers, i.e., enhancers that have a molecular weight in the range of about 150 to 1000, an aqueous solubility of less than about 1 wt. %, preferably less than about 0.5 wt. %, and most preferably less than about 0.2 wt. %. The Hildebrand solubility parameter δ of plasticizing enhancers is in the range of about 2.5 to about 10, preferably in the range of about 5 to about 10. Preferred lipophilic enhancers are fatty esters, fatty alcohols, and fatty ethers. Examples of specific and most preferred fatty acid esters include methyl laurate, ethyl oleate, propylene glycol monolaurate, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, preferably a $C_2$-$C_4$ alkane diol or triol, are substituted with one or two fatty ether substituents.

Additional permeation enhancers will be known to those of ordinary skill in the art of topical drug delivery, and/or are described in the pertinent texts and literature. See, e.g., *Percutaneous Penetration Enhancers*, eds. Smith et al. (CRC Press, 1995).

Various other additives may be included in the compositions of the present invention in addition to those identified above. These include, but are not limited to, antioxidants, astringents, perfumes, preservatives, emollients, pigments, dyes, humectants, propellants, and sunscreen agents, as well as other classes of materials whose presence may be pharmaceutically or otherwise desirable. Typical examples of optional additives for inclusion in the formulations of the invention are as follows: preservatives such as sorbate; solvents such as isopropanol and propylene glycol; astringents such as menthol and ethanol; emollients such as polyalkylene methyl glucosides; humectants such as glycerine; emulsifiers such as glycerol stearate, PEG-100 stearate, polyglyceryl-3 hydroxylauryl ether, and polysorbate 60; sorbitol and other polyhydroxyalcohols such as polyethylene glycol; sunscreen agents such as octyl methoxyl cinnamate (available commercially as Parsol MCX) and butyl methoxy benzoylmethane (available under the tradename Parsol 1789); antioxidants such as ascorbic acid (vitamin C), α-tocopherol (Vitamin E), β-tocopherol, γ-tocopherol, δ-tocopherol, ε-tocopherol, $ζ_1$-tocopherol, $ζ_2$-tocopherol, η-tocopherol, and retinol (vitamin A); essential oils, ceramides, essential fatty acids, mineral oils, vegetable oils (e.g., soya bean oil, palm oil, liquid fraction of shea butter, sunflower oil), animal oils (e.g., perhydrosqualene), synthetic oils, silicone oils or waxes (e.g., cyclomethicone and dimethicone), fluorinated oils (generally perfluoropolyethers), fatty alcohols (e.g., cetyl alcohol), and waxes (e.g., beeswax, carnauba wax, and paraffin wax); skin-feel modifiers; and thickeners and structurants such as swelling clays and crosslinked carboxypolyalkylenes that may be obtained commercially under the Carbopol® trademark.

Other additives include beneficial agents such as those materials that condition the skin (particularly, the upper layers of the skin in the stratum corneum) and keep it soft by retarding the decrease of its water content and/or protect the skin. Such conditioners and moisturizing agents include, by way of example, pyrrolidine carboxylic acid and amino acids; organic antimicrobial agents such as 2,4,4'-trichloro-2-hydroxy diphenyl ether (triclosan) and benzoic acid; anti-inflammatory agents such as acetylsalicylic acid and glycyrrhetinic acid; anti-seborrhoeic agents such as retinoic acid; vasodilators such as nicotinic acid; inhibitors of melanogenesis such as kojic acid; and mixtures thereof. Further additional active agents including, for example, alpha hydroxyacids, alpha ketoacids, polymeric hydroxyacids, moisturizers, collagen, marine extract, and antioxidants such as ascorbic acid (vitamin C), α-tocopherol (Vitamin E), β-tocopherol, γ-tocopherol, δ-tocopherol, ε-tocopherol, $ζ_1$-tocopherol, $ζ_2$-tocopherol, η-tocopherol, and retinol (vitamin A), and/or pharmaceutically acceptable salts, esters, amides, or other derivatives thereof. A preferred tocopherol compound is α-tocopherol. Additional agents include those that are capable of improving oxygen supply in skin tissue, as described, for example, in Gross, et al, WO 94/00098 and Gross, et al, WO 94/00109, both assigned to Lancaster Group AG (incorporated herein by reference). Sunscreens may also be included.

Other embodiments may include a variety of non-carcinogenic, non-irritating healing materials that facilitate treatment with the formulations of the invention. Such healing materials may include nutrients, minerals, vitamins, electrolytes, enzymes, herbs, plant extracts, glandular or animal extracts, or safe therapeutic agents that may be added to the formulation to facilitate the healing of dermal disorders.

The amounts of these various additives are those conventionally used in the cosmetics field, and range, for example, from about 0.01% to about 20% of the total weight of the topical formulation.

The formulations of the invention may also include conventional additives such as opacifiers, fragrance, colorant, stabilizers, surfactants, and the like. In certain embodiments, other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

The formulations may also contain irritation-mitigating additives to minimize or eliminate the possibility of skin irritation or skin damage resulting from the chemical entity to be administered, or other components of the composition. Suitable irritation-mitigating additives include, for example: α-tocopherol; monoamine oxidase inhibitors, partic ularly phenyl alcohols such as 2-phenyl-1-ethanol; glycerin; salicylates; ascorbates; ionophores such as monensin; amphiphilic amines; ammonium chloride; N-acetylcysteine; capsaicin; and chloroquine. The irritation-mitigating additive, if present, may be incorporated into the compositions at a concentration effective to mitigate irritation or skin damage, typically representing not more than about 20 wt. %, more typically not more than about 5 wt. %, of the formulation.

Further suitable pharmacologically active agents that may be incorporated into the present formulations in certain embodiments and thus topically applied along with the active agent include, but are not limited to, the following: agents that improve or eradicate pigmented or non-pigmented age spots, keratoses, and wrinkles; antimicrobial agents; antibacterial agents; antipruritic and antixerotic agents; antiinflammatory agents; local anesthetics and analgesics; corticosteroids; retinoids; vitamins; hormones; and antimetabolites.

Some examples of topical pharmacologically active agents include acyclovir, amphotericins, chlorhexidine, clotrimazole, ketoconazole, econazole, miconazole, metronidazole, minocycline, nystatin, neomycin, kanamycin, phenytoin, para-amino benzoic acid esters, octyl methoxycinnamate, octyl salicylate, oxybenzone, dioxybenzone, tocopherol, tocopheryl acetate, selenium sulfide, zinc pyrithione, diphenhydramine, pramoxine, lidocaine, procaine, erythromycin, tetracycline, clindamycin, crotamiton, hydroquinone and its monomethyl and benzyl ethers, naproxen, ibuprofen, cromolyn, retinol, retinyl palmitate, retinyl acetate, coal tar, griseofulvin, estradiol, hydrocortisone, hydrocortisone 21-acetate, hydrocortisone 17-valerate, hydrocortisone 17-butyrate, progesterone, betamethasone valerate, betamethasone dipropionate, triamcinolone acetonide, fluocinonide, clobetasol propionate, minoxidil, dipyridamole, diphenylhydantoin, benzoyl peroxide, and 5-fluorouracil, A cream, lotion, gel, ointment, paste or the like may be spread on the affected surface and gently rubbed in. A solution may be applied in the same way, but more typically will be applied with a dropper, swab, or the like, and carefully applied to the affected areas.

The application regimen will depend on a number of factors that may readily be determined, such as the severity of the condition and its responsiveness to initial treatment, but will normally involve one or more applications per day on an ongoing basis. One of ordinary skill may readily determine the optimum amount of the formulation to be administered, administration methodologies and repetition rates. In general, it is contemplated that the formulations of the invention will be applied in the range of once or twice weekly up to once or twice daily.

BRIEF DESCRIPTION OF THE FIGURES

The invention will be further described in the following examples with reference to the figures in which.

EXAMPLES

In this study we differentiated normal human epidermal keratinocytes in cell culture inserts, and investigated the effect of betaine and probiotics, either soluble metabolites, whole bacterial cells or bacterial cell lysates on barrier characteristics. Transepithelial electrical resistance (TEER) is widely used in epithelial cell studies to measure the tight junction integrity. TEER reflects the transepithelial permeability of water-soluble ions, and a higher TEER indicates a lower ionic permeability. Moreover, we studied the expression of the claudin-4, occludin and zonula occludens-1 in these cells.

Material and Methods

Keratinocyte Differentiation

Adult normal human primary keratinocytes (Invitrogen, Carlsbad, Calif., USA) were maintained in EpiLife® medium with 60 µM calcium (Invitrogen) supplemented with Human Keratinocyte Growth Supplement (HKGS) (Invitrogen) (basal medium) at 5% $CO_2$ atmosphere. To differentiate the keratinocytes, the P5-P7 cells were plated on ThinCert™ cell culture inserts (Greiner Bio-one, Frickenhausen, Germany) at density of $10^5$ cells/cm². After overnight incubation at 5% $CO_2$ atmosphere the basal medium was aspirated and changed to differentiation medium (DM) consisting of EpiLife® medium with 1.45 mM $CaCl_2$ supplemented with human keratinocyte growth supplement and incubated for 4 days at 5% $CO_2$ atmosphere. DM was changed both at both the apical and basolateral side every day. Test substances were given at fourth day after starting the differentiation.

Experiments with Differentiated Keratinocytes

Betaine (Danisco) were dissolved in DM, and applied to apical side of differentiated keratinocytes at amounts of 0, 10, 50, 100, 250 and 500 µM. The cells were incubated for 1, 12, and 24 hours at which points TEER was measured as described below.

*Lactobacillus acidophilus* NCFM® (ATCC 700396), *Bifidobacterium lactis* 420 DSM22089 (commercially available from Danisco A/S), *L. acidophilus* La-14 (ATCCSD5212) (commercially available from Danisco A/S), *L. salivarius* Ls-33 (ATCCSD5208) and *Propionibacterium jensenii* P63 (DSM 22192)(Danisco Cultures, Paris, France) were cultured anaerobically at 37° C. in de Man, Rogosa and Sharpe (MRS) broth (LabM, Bury, United Kingdom). For experiments with soluble probiotic metabolites the bacteria were cultivated to OD600≈0.6-0.9, and for experiments with whole bacterial cells the cultivation continued until the exponential growth rate of bacteria was achieved. The bacterial cell densities were determined with flow cytometry (FACSCalibur, Becton Dickinson, San Jose, Calif., USA). Bacterial cells were removed from the soluble metabolites by centrifuging 25° C., 5 min, 3000×g. Bacterial pellets were discarded, and supernatant containing soluble metabolites was diluted to 10% (vol/vol) in DM, sterile-filtered with 0.2 µm sterile syringe filter units (Sartorius, Goettingen, Germany). Bacterial cells were washed once with DM, and administered as 100 bacterial cells towards one keratinocyte suspended in DM.

For studies with bacterial cell lysates the bacterial cells were sheared with Precellys 24 bead beater (Bertin Technologies, Saint-Quentin-en-Yvelines Cedex, France) with grinding kit VK01 (Bertin Technologies) at 6500 rpm with 3 cycles of 45 seconds. The breakdown of the cells was confirmed by light microscopy. The bacterial cell lysates suspended in DM were sterile-filtered with 0.2 µm syringe units (Sartorius) before applying them to the apical side of the differentiated keratinocytes at an amount that corresponded to 100 lysed bacterial cells to one keratinocyte.

The differentiated keratinocytes were treated with soluble metabolites produced by probiotics, probiotic whole bacterial cells, and bacterial cell lysates from the apical side for 1 h, 8 h and 24 h at which the TEER was measured. As a control for experiments with soluble metabolites 10% bacterial culture media was used. At the end of each experiment at 24 h time point the keratinocytes were lysed for RNA isolation (see below). In some of the experiments baseline TEER decreased towards the 24 h treatment period due to probably variation in the cell amount plated in the insert.

Measurement of TEER

The integrity of the monolayer was verified by measuring TEER before and after each time point using Millicell-ERS system (Millipore, Billerica, Mass., US) (26). The TEER obtained from the monolayer and the insert was subtracted with background TEER obtained from the insert to yield the monolayer resistance and multiplied with the area of the insert to obtain the result as ohm×cm². For the experiments with betaine and probiotics the results are expressed as a percentage change in TEER (% Change in TEER) which reflects the change in the resistance in the given time point compared to a control time point, which was the same cell monolayer before applying the test substances.

RNA Isolation and cDNA synthesis

The medium was aspirated after day 1, 2, 3 and 4 along the keratinocyte differentiation process, or at the end of the experiment after 24 hours for the experiments with betaine or probiotics, and the cells were lysed immediately with buffer RA1 supplemented with 1% β-mercaptoethanol (Sigma-Aldrich, St. Louis, Mo., USA). Total RNA was isolated using NucleoSpin® 96 RNA kit (Macherey Nagel GmbH & Co. KG, Düren, Germany). Reverse-transcription was done using SuperScript III (Invitrogen, Carlsbad, Calif., US) with random primers (Invitrogen).

Real-Time Quantitative PCR

Real-time quantitative PCR of claudin-4 (CLDN4), occludin (OCLN), zonula occludens-1 (ZO-1) was done with TaqMan gene expression assays (Applied biosystems, Foster City, Calif., USA) designed for each specific gene in an amplification reaction of 20 µl according to manufacturer's instructions with 7500 Fast Real-time PCR System (Applied Biosystems). As an endogenous control gene ribosomal protein, large, P0 (RPLP0) was quantified in parallel in each experiment (27, 28). The expression of RPLP0 was first tested with extensive set of differentially treated samples, and its expression was found to be constant in various treatments (data not shown). The data was analyzed by using the $2^{-\Delta\Delta C_t}$ method (29), and the results are expressed as fold increase of mRNA amount of the unknown samples relative to the mRNA amount obtained for the sample at day 1 for keratinocyte differentiation, or for untreated control samples for experiments with betaine and probiotics.

Statistical Analyses

The statistical significance of differences between treatments were determined using one-way ANOVA. P-values of 0.05 or less were considered as significant. All comparisons were made against the respective medium-only controls unless otherwise stated. Correlation of the TEER and the expression of tight junction components during keratinocyte differentiation was tested with Pearson correlation calculation. All analyses were calculated using GraphPad Prism version 5.01. Mean±SE values are shown for all the results.

Results

Differentiation of Keratinocytes Increased Tight Junction Integrity and Expression of Claudin-4

Figure 1:
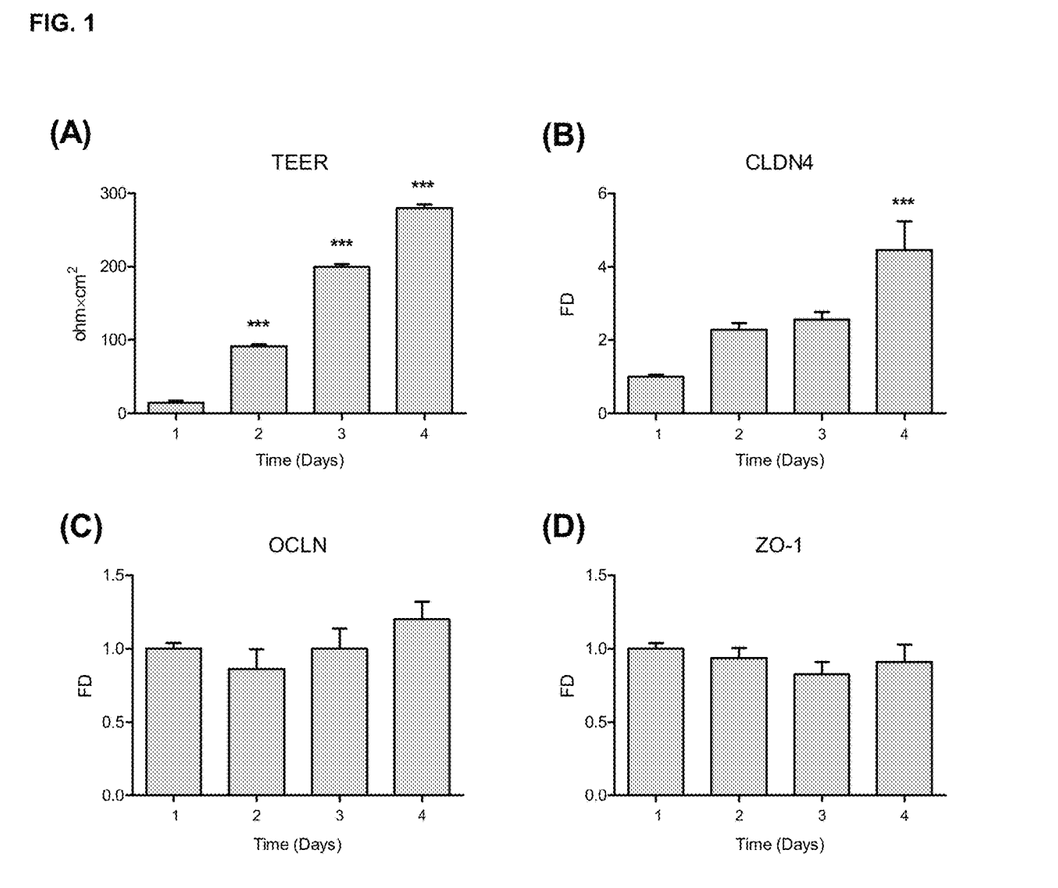
FIG. 1 shows the increase in transepithelial electrical resistance (TEER) in keratinocytes during the dufferentiation of keratinocyte. (A). Expression of claudin-4 (CLDN4) (A), occludin (OCLN) (B) and zonula occludens-1 (ZO-1) (C) during the differentiation of keratinocytes. Mean±SE shown, *** $p<0.001$, compared to 1-day sample).

Normal primary human keratinocytes isolated from adults were differentiated on cell culture inserts in order to follow the tight junction formation between the epithelial cells by measuring transepithelial electric resistance (TEER). Differentiation of human adult primary keratinocytes in cell culture inserts increased the TEER by 84%, 93% and 95% at day 2, 3, and 4 from the start of the study (p<0.001 at all time points compared to day 1) (FIG. 1). The increase in TEER was time-dependent with Pearson r=0.7556 (p=0.0003).

During the 4-day differentiation process the gene expression of tight junction components CLDN4, OCLN, and ZO-1 in the keratinocytes was studied. The expression of OCLN and ZO-1 remained at basal level throughout the differentiation process, whereas the expression of CLDN4 increased (FIG. 1b) (p<0.001 at day 4; compared today 1). The TEER values correlated positively with CLDN4 expression (p<0.001, Pearson r=0.8093), whereas no correlation between TEER and ZO-1 expression or TEER and OCLN expression was observed.

Betaine Increased Keratinocyte Tight Junction Integrity and Decreased the Expression of Occludin.

Figure 2:
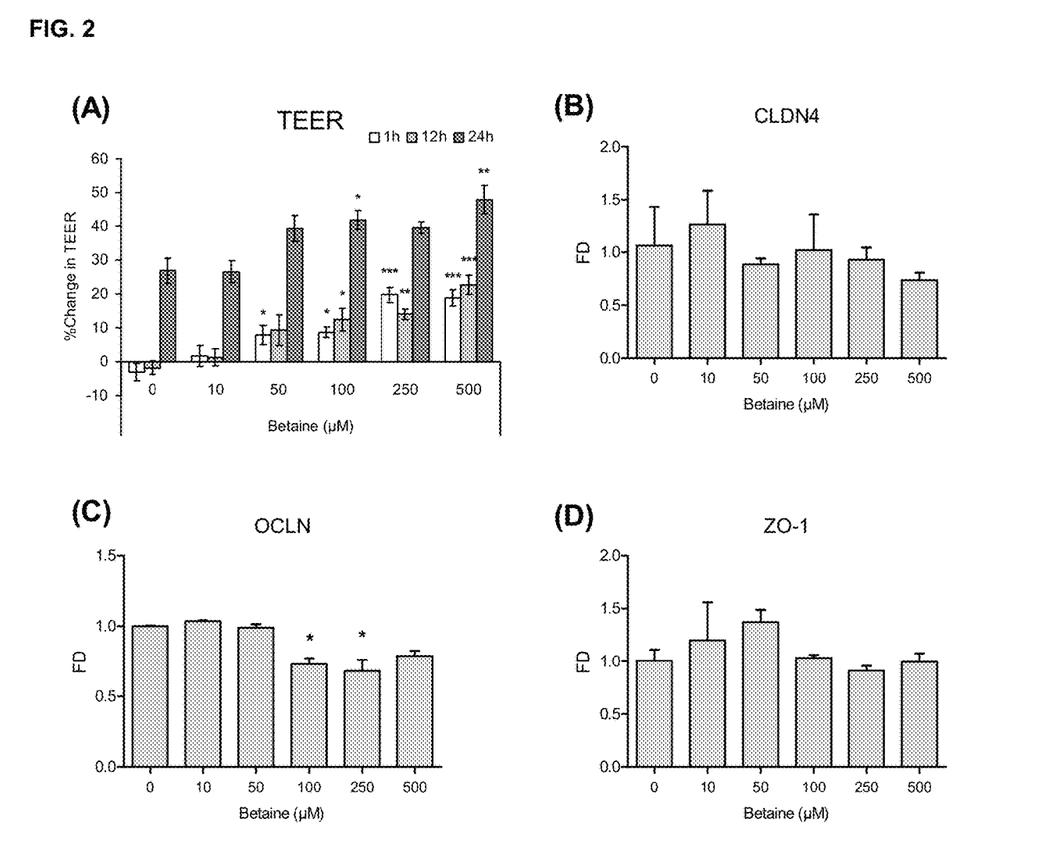
FIG. 2 shows regulation of transepithelial electrical resistance (TEER) in keratinocytes treated with 0, 10, 50, 100, 250 and 500 µM of betaine for 1 h, 12 h and 24 h (A). Expression of claudin (CLDN4) (B), occludin (OCLN) (C) and zonula occludens-1 (ZO-1) (D) in keratinocytes after 24 h treatment with 0, 10, 50, 100, 250 and 500 µM of betaine. Mean±SE shown, * $p<0.05$, compared to sample with no betaine.

The effect of betaine on differentiated keratinocytes was studied by incubating the cells for 1, 12, and 24 hours from the apical side with 0, 10, 50, 100, 250 and 500 µM of betaine. TEER remained at the basal level with the lowest amount of betaine, but increased after 1 hour with 50 µM betaine (p<0.05) throughout the higher concentrations, and remained increased still after 12 h (p<0.05 to p<0.001) (FIG. 2a). The baseline TEER increased at 24 h, and only 100 µM and 500 µM amounts of betaine showed an additional increase in TEER of 41.8±2.8% and 47.8±4.2%, respectively (p<0.05 and p<0.01, respectively).

The expression of CLDN4 (FIG. 2b), OCLN (FIG. 2c) and ZO-1 (FIG. 2d) in the cells incubated 24 h 0, 10, 50, 100, 250 and 500 µM of betaine was determined. The expression of CLDN4, and ZO-1 remained similar to the basal levels in the betaine-treated samples. Moreover, expression of OCLN decreased in samples treated with 100, and 250 µM betaine (p<0.05). In contrast to the baseline differentiation in this data set, the amount of OCLN also correlated negatively with TEER (p<0.05, Pearson r=−0.6214).

Probiotics Increased Keratinocyte Tight Junction Integrity.

The differentiated keratinocytes were treated with soluble probiotic metabolites, whole probiotic bacterial cells or probiotic bacterial cell lysates for 1 h, 8 h, and 24 h.

Figure 3:
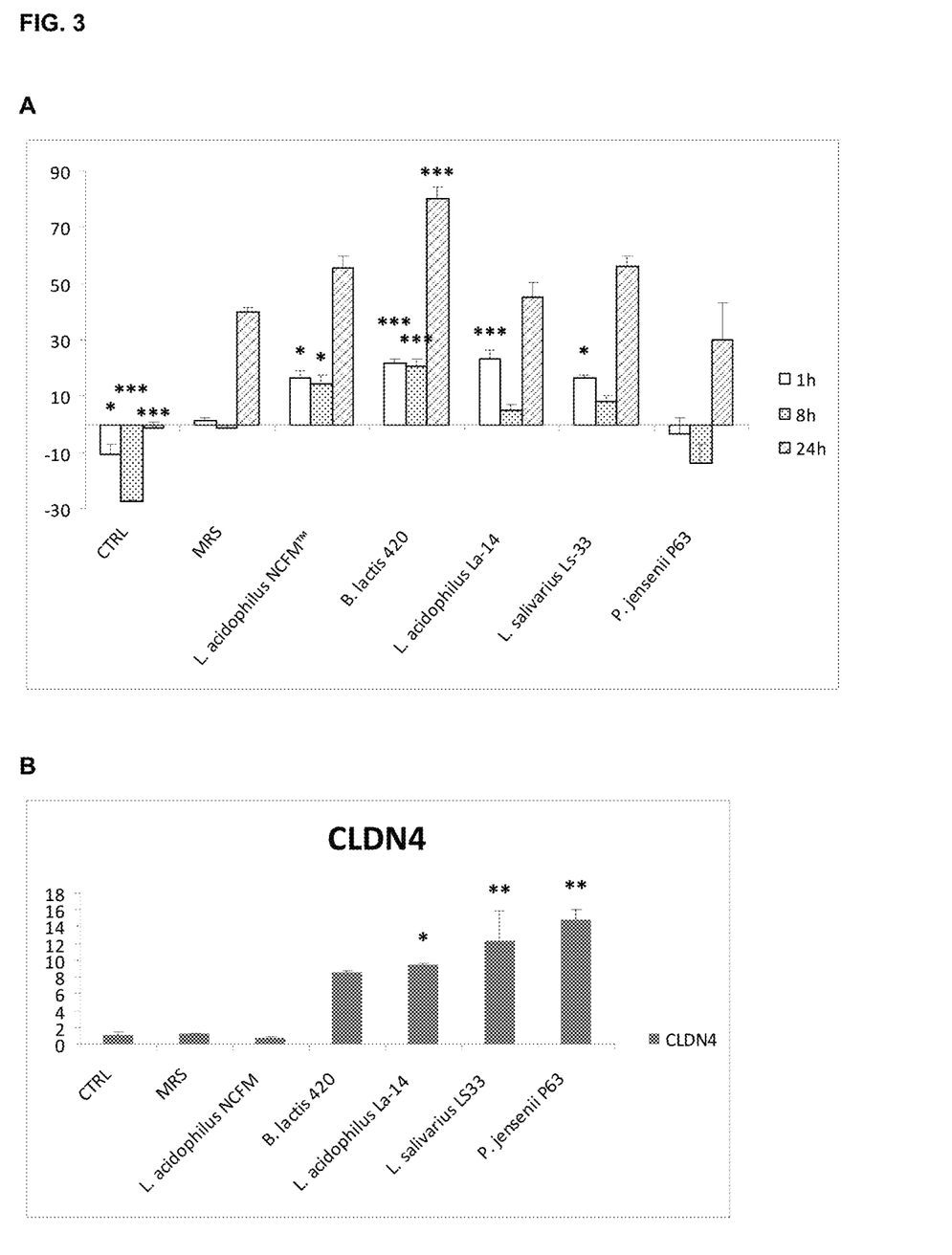
FIG. 3 shows regulation of transepithelial electrical resistance (TEER) in keratinocytes treated with medium (CTRL), 10% (vol/vol) de Man, Rogosa and Sharpe (MRS) broth used to cultivate the probiotics, and 10% (vol/vol) soluble probiotic metabolites for 1 h, 8 h and 24 h (A). Expression of claudin (CLDN4) (B), occludin (OCLN) (C) and zonula occludens-1 (ZO-1) (D) in keratinocytes after 24 h treatment with medium (CTRL), 10% (vol/vol) de Man, Rogosa and Sharpe (MRS) broth used to cultivate the probiotics, and 10% (vol/vol) soluble probiotic metabolites for 24 h. Mean±SE shown, * $p<0.05$;  $p<0.01$; * $p<0.001$.

Compared to 10% bacterial culture media control (MRS), soluble metabolites samples increased the TEER values (FIG. 3a). At 1 h time point the TEER increased with all tested soluble metabolites with an exception of *P. jensenii* P63 produced soluble metabolites, which did not increase the TEER above the level of the 10% bacterial culture media control. The highest increase in TEER with probiotic soluble metabolites was observed with the *B. lactis* 420 soluble metabolites, that increased TEER 20.4%±2.8% ($p<0.001$) at 8 h, and 80.3%±3.8% ($p<0.001$) at 24 h.

Figure 4:
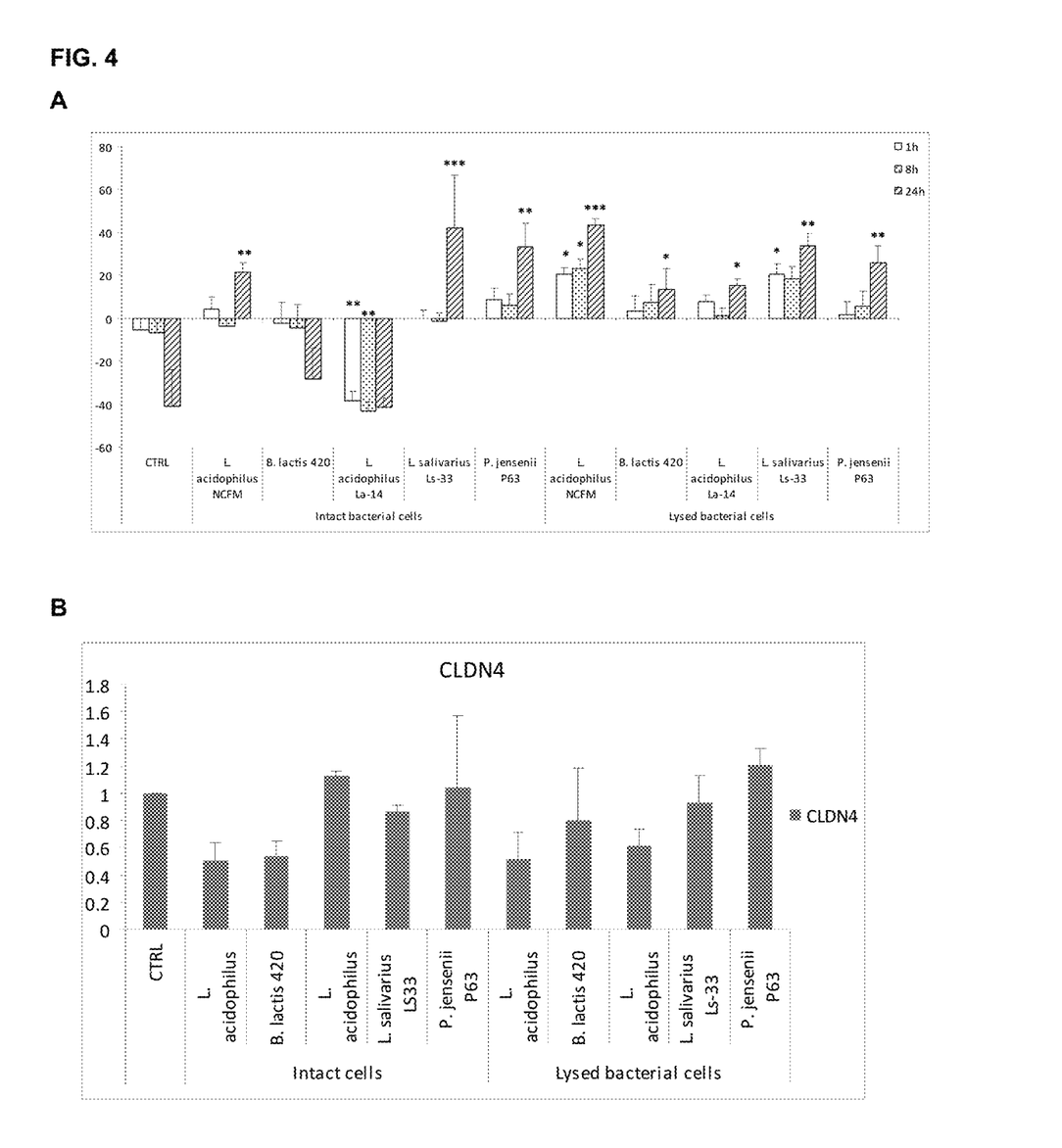
FIG. 4 shows regulation of transepithelial electrical resistance (TEER) in keratinocytes treated with medium (CTRL), probiotic whole cells or probiotic cell lysates for 1 h, 8 h and 24 h (A). Expression of claudin (CLDN4) (B), occludin (OCLN) (C) and zonula occludens-1 (ZO-1) (D) in keratinocytes after 24 h treatment with medium (CTRL), medium (CTRL), probiotic whole cells or probiotic cell lysates for 24 h. Mean±SE shown, * $p<0.05$;  $p<0.01$; * $p<0.001$.

The incubation of keratinocytes with whole bacterial cells showed an increase in TEER (FIG. 4a). TEER remained at the basal level in keratinocytes treated by *L. acidophilus* NCFM®, *L. salivarius* Ls-33, and *P. jensenii* P63 at 1 h and at 8 h. At 24 h the baseline TEER value of the control was noticeably decreased from the value observed before the start of the experiment. However, in *L. acidophilus* NCFM® (21.4%±4.4%, $P<0.01$), *L. salivarius* Ls-33 (42.2%±24.4%, $p<0.001$), and *P. jensenii* P63 (33.1±11.3%, $p<0.01$) the increased TEER above the baseline at 24 h was significant. In contrast, in keratinocytes treated with *L. acidophilus* La-14 the TEER decreased below the baseline significantly already at 1 h time point (−38.3%±4.4%, $p<0.01$), and remained decreased throughout the whole experiment (−43.8±4.7%, $p<0.01$ at 8 h, and −41.3%±4.1%, non-significant at 24 h).

In the keratinocytes treated with bacterial cell lysates (FIG. 4a) no similar decrease in TEER was observed in the samples treated with *L. acidophilus* La-14, and *B. lactis* 420 lysates as was observed in keratinocytes treated with respective whole cells. However, compared to other probiotics these aforementioned as well as *P. jensenii* P63 lysate had a smaller effect, as the TEER increased significantly only after 24 h (15.2%±3.3% for *L. acidophilus* La-14 lysate $p<0.05$; 13.5%±9.6% for *B. lactis* 420 lysate $p<0.05$; 25.7%±8.0% for *P. jensenii* P63 lysate $p<0.01$). *L. acidophilus* NCFM® lysate and *L. salivarius* Ls-33 lysate had a stronger effect since they induced an increase in TEER already after 1 h (20.4%±3.2% $p<0.05$, and 20.5%±4.9% $p<0.05$, respectively), that remained elevated at 8 h (23.4%±4.1%, $p<0.05$, and 18.3%±5.7% nonsignificant, respectively), and at 24 h (43.6%±3.0%, $p<0.001$, and 33.8%±5.6%, $p<0.01$).

Probiotics Affected the Keratinocyte Tight Junction Protein Expression Strain-Dependently The expression of the TJ protein CLDN4, OCLN, and ZO-1 from the cells treated 24 h with soluble metabolites produced by the probiotics, whole probiotic bacteria as well as cell lysates was determined.

In the case of soluble metabolites treated keratinocytes gene expression changes beyond the changes in bacterial culture media control was observed in the case of CLDN4 (FIG. 3b) but not with OCLN (FIG. 3c) or ZO-1 (FIG. 3d). The soluble metabolites produced by three of the probiotics strains increased CLDN4 expression in soluble metabolites treated keratinocytes: *L. acidophilus* La-14 (Fold difference (FD)=9.4±0.3, $p<0.05$, compared to bacterial culture media), *L. salivarius* Ls-33 (FD=12.4±3.5, $p<0.01$, compared to bacterial culture media), and *P. jensenii* P63 (FD=14.8±1.3, $p<0.01$, compared to bacterial culture media). *B. lactis* 420 soluble metabolites has also tendency to increase CLDN4 expression (FD=8.6±0.05), but it did not reach significance. The expression of CLDN4 did not show correlation to TEER values, but a weak correlation was observed between ZO-1 and TEER (Pearson r=−0.5851, $p<0.05$).

In the case of whole bacterial cell treated keratinocytes, no effect on regulation of CLDN4 (FIG. 4b), OCLN (FIG. 4c) or ZO-1 (FIG. 4d) was observed in these cells, as well as no correlation to the TEER values.

However, when bacterial cell lysates were used to treat the cells, *L. acidophilus* NCFM® lysate was observed to up-regulate OCLN expression (FIG. 4c) (FD=2.1±0.3, $p<0.001$), and ZO-1 expression (FD=2.8±0.2, $p<0.01$). From all the bacterial cell lysates *B. lactis* 420 lysate was also able to increase the ZO-1 expression (FD=2.5±0.3, $p<0.05$). No correlation between CLDN4, and ZO-1 and TEER was observed in bacterial cell lysates treated cells but a correlation between TEER and OCLN expression was observed (Pearson r=0.7107, $p<0.05$).

Discussion

The tight junctions form a part of the epithelial permeability barrier between the normal human epidermal keratinocyte cells in culture. Permeation of solutes through the intact TJ can be quantified by transepithelial electrical resistance. In immunofluorescence studies, differentiation of keratinocytes by a high $Ca^{2+}$ concentration induced translocation of occludin, claudin-1, and claudin-4 to overlapping continuous lines circumscribing individual cells, indicating that the proteins localized to TJs. We observed that the expression of occludin, and ZO-1 were constant during the Ca2+ induced differentiation io of the epidermal keratinocytes, but the expression of claudin-4 increased steadily. Previously it has been documented, that when TJ structure and permeability barrier was disrupted with ochratoxin A in normal human keratinocytes, the expression of claudin-4 was reduced.

In a comparative study betaine was shown to increase the TEER values but did not affect the expression of the tight junction proteins studied here other than occludin. Removal of occludin by siRNA technique resulted in decreased TEER (36), but knock-out of occludin in mice do not alter the epidermal barrier function (37) and it is quite possible that reduced expression of occludin is not linked with increased TEER in betaine-treated keratinocytes even though a weak negative correlation between occludin and TEER was observed. An increase in TEER indicates that betaine improves tight junction integrity, and could contribute to the inside-outside barrier and hydration status of the skin also through this mechanism additionally to its osmolyte function. The function of organic osmolytes in regulation of barrier integrity is also indicated by studies with taurine and betaine which reduced the irritating effects of surfactants in epidermis (44).

Previous studies with probiotics have concentrated on either systemic or gastrointestinal effects.

Soluble metabolites produced by probiotics were observed to affect TEER and expression of tight junction proteins differentially compared to whole probiotic cells or probiotic cell lysates, a phenomenon that has also been reported for intestinal epithelial cells. In this study, expression of claudin-4 was regulated strongly by soluble metabolites produced by probiotics in a strain-specific manner but not by whole probiotic cells or their lysates.

In this study, up regulation of occludin was observed with the probiotic *L. acidophilus* NCFM® cell lysate, in contrast to down regulation with betaine. *L. acidophilus* NCFM® lysate was able to regulate another TJ gene, ZO-1, which was also up regulated also by *B. lactis* 420. ZO-1 and occludin have been observed previously to be regulated by probiotics in intestinal epithelial cells, and it has been shown that leaky gut was prevented in dextran sodium sulfate-induced colitis in mice by a probiotic *E. coli* Nissle 1917 through upregulation of ZO-1 expression (51). ZO-1 has been shown to stabilize the TJ barrier through a link between the barrier and perijunctional actomyosin cytoskeleton (30). The probiotic cell lysates increased the TEER values.

The topical application of probiotics would only affect the uppermost skin layers, and thus, in order to achieve penetration into the deeper layers, the cell lysates or soluble metabolites may be better.

Tight junctions are important not only as barrier against free diffusion of fluids, electrolytes and macromolecules, but also against the translocation of surface associated microorganisms and their secreted products (Sousa et al 2005). Probiotic bacterial cell lysates could be a used to enhance this barrier without inducing pathological immune responses.

In conclusion we show that betaine, and probiotics are able to improve TJ integrity between normal human epidermal keratinocytes. Enhancement of the skin barrier may be important particularly in diseases where barrier function is impaired.

It is to be understood that while the invention has been described in conjunction with the preferred specific embodiments thereof, the foregoing description is intended to illustrate and not limit the scope of the invention.

Other aspects, advantages, and modifications will be apparent to those skilled in the art to which the invention pertains.

REFERENCE LIST (1) Honari S. Topical therapies and antimicrobials in the management of burn wounds. Crit Care Nurs Clin North Am 2004; 16:1-11.
(2) Proksch E, Brandner J M, Jensen J M. The skin: an indispensable barrier. Exp Dermatol 2008; 17:1063-72.
(3) Lee S H, Jeong S K, Ahn S K. An update of the defensive barrier function of skin. Yonsei Med J 2006; 47:293-306.
(4) Furuse M, Hata M, Furuse K, Yoshida Y, Haratake A, Sugitani Y, et al. Claudin-based tight junctions are crucial for the mammalian epidermal barrier: a lesson from claudin-1-deficient mice. J Cell Biol 2002; 156: 1099-111.
(5) Brandner J M. Tight junctions and tight junction proteins in mammalian epidermis. European Journal of Pharmaceutics and Biopharmaceutics 2009; 72:289-94.
(6) Pummi K, Malminen M, Aho H, Karvonen S L, Peltonen J, Peltonen S. Epidermal tight junctions: ZO-1 and occludin are expressed in mature, developing, and affected skin and in vitro differentiating keratinocytes. J Invest Dermatol 2001; 117:1050-8.
(8) Sousa S, Lecuit M, Cossart P. Microbial strategies to target, cross or disrupt epithelia. Curr Opin Cell Biol 2005; 17:489-98.
(9) Holgate S T. Epithelium dysfunction in asthma. J Allergy Clin Immunol 2007; 120:1233-44.
(10) Yamamoto T, Kurasawa M, Hattori T, Maeda T, Nakano H, Sasaki H. Relationship between expression of tight junction-related molecules and perturbed epidermal barrier function in UVB-irradiated hairless mice. Arch Dermatol Res 2008; 300:61-8.
(13) FAO/WHO. Guidelines for the evaluation of probiotics in food. http://www.who.int/foodsafety/publications/fs_ management/probiotics2/ en/_2002 p. 1-11.
(17) Ouwehand A, Nermes M, Collado M, Rautonen N, Salminen S, Isolauri E. Specific probiotics alleviate allergic rhinitis during the birch pollen season. World Journal of Gastroenterology 2009; 15:3261-8.
(22) Di Marzio L, Cinque B, De Simone C, Cifone M G. Effect of the lactic acid bacterium Streptococcus thermophilus on ceramide levels in human keratinocytes in vitro and stratum corneum in vivo. Journal of Investigative Dermatology 1999; 113:98-106.
(26) Chen Y H, Lu Q, Goodenough D A, Jeansonne B. Nonreceptor tyrosine kinase c-Yes interacts with occludin during tight junction formation in canine kidney epithelial cells. Mol Biol Cell 2002; 13:1227-37.
(27) Bar M, Bar D, Lehmann B. Selection and Validation of Candidate Housekeeping Genes for Studies of Human Keratinocytes—Review and Recommendations. Journal of Investigative Dermatology 2009; 129: 535-7.
(28) Minner F, Poumay Y. Candidate Housekeeping Genes Require Evaluation before their Selection for Studies of Human Epidermal Keratinocytes. Journal of Investigative Dermatology 2009; 129:770-3.
(29) Livak K J, Schmittgen T D. Analysis of relative gene expression data using real-time quantitative PCR and the 2(-Delta Delta C(T)) Method. Methods 2001; 25:402-8.
(30) Van Itallie C M, Fanning A S, Bridges A, Anderson J M. ZO-1 stabilizes the tight junction solute barrier through coupling to the perijunctional cytoskeleton. Mol Biol Cell 2009; 20:3930-40.
(36) Yamamoto T, Saeki Y, Kurasawa M, Kuroda S, Arase S, Sasaki H. Effect of RNA interference of tight junction-related molecules on intercellular barrier function in cultured human keratinocytes. Arch Dermatol Res 2008; 300:517-24.
(37) Saitou M, Furuse M, Sasaki H, Schulzke J D, Fromm M, Takano H, et al. Complex phenotype of mice lacking occludin, a component of tight junction strands. Mol Biol Cell 2000; 11:4131-42.
(44) Nicander I, Rantanen I, Rozell B L, Soderling E, Ollmar S. The ability of betaine to reduce the irritating effects of detergents assessed visually, histologically and by bioengineering methods. Skin Res Technol 2003; 9:50-8.
(51) Ukena S N, Singh A, Dringenberg U, Engelhardt R, Seidler U, Hansen W, et al. Probiotic Escherichia coli Nissle 1917 inhibits leaky gut by enhancing mucosal integrity. PLoS One 2007; 2:e1308.

The invention claimed is:

1. A method for treating a disorder associated with Tight Junction function in a patient in need thereof, wherein:
   the method comprises topically administering a formulation comprising an effective amount of a probiotic bacteria, a soluble metabolite of a probiotic bacteria and/or a cell lysate of a probiotic bacteria;
   the probiotic bacteria is *Propionibacterium jensenii P63*; and
   the disorder is selected from the group consisting of psoriasis, acne, atopic dermatitis, dry skin, allergy, rashes, UV-irritated skin, detergent irritated skin, thinning skin and asthma.

2. The method according to claim 1, wherein the formulation is formulated for administration to the skin.

3. The method according to claim 1, wherein:
   the formulation is formulated for administration to a mucous membrane, and
   said mucous membrane is selected from the group consisting of mucosa of a vagina, penis, urethra, the bladder, anus, mouth, nose, throat, bronchi, lungs, eye and ear.

4. The method according to claim 1, wherein the formulation comprises a second probiotic bacteria, soluble metabolite of a second probiotic bacteria and/or cell lysate of a second probiotic bacteria.

5. The method according to claim 4, wherein the second probiotic bacteria is a lactic acid bacteria.

6. The method according to claim 4, wherein the second probiotic bacteria is selected from the group consisting of *Lactobacillus acidophilus, Lactobacillus salivarius, Bifidobacterium lactis* and *Propionibacterium jensenii*.

7. The method according to claim 1, wherein the formulation comprises the probiotic bacteria and/or a cell lysate of the probiotic bacteria.

8. The method according to claim 1, wherein the formulation further comprises betaine, a polyol and/or a polyphenol.

9. The method according to claim 1, wherein the disorder is selected from the group consisting of psoriasis, acne, atopic dermatitis, dry skin, allergy, rashes, UV-irritated skin, detergent irritated skin and thinning skin.

10. The method according to claim 1, wherein the formulation further comprises a pharmaceutically acceptable carrier.

11. The method according to claim 1, wherein the formulation comprises between about 0.01% and about 30% by weight of the probiotic bacteria, soluble metabolite and/or cell lysate.

12. The method according to claim 1, wherein the formulation is in a form of a cream, lotion, spray, solution, gel, ointment, paste, plaster, paint, bioadhesive or suspension.

13. The method according to claim 11, wherein the formulation comprises liposomes, micelles, and/or microspheres.

14. The method according to claim 1, wherein the method comprises topically administering to the patient the probiotic bacteria.

15. The method according to claim 14, wherein the method comprises topically administering from $10^6$ to $10^{12}$ CFU of the probiotic bacteria per day.

16. The method according to claim 1, wherein the method comprises topically administering to the patient a cell lysate of the probiotic bacteria.

17. The method according to claim 1, wherein the method comprises topically administering to the patient a soluble metabolite of the probiotic bacteria.

18. The method according to claim 1, wherein the formulation further comprises xylitol or lactitol.

19. The method according to claim 1, wherein the formulation further comprises epicatechin or gallocatechin.

20. The method according to claim 1, wherein the disorder is irritated skin caused by enzymes used in a washing detergent or sodium lauryl sulphate.

21. The method according to claim 1, wherein the disorder is thinning skin of an elderly person.

22. The method according to claim 1, wherein the disorder is thinning skin of a child.

23. The method according to claim 1, wherein the patient is a human.

* * * * *